(12) United States Patent
Millette et al.

(10) Patent No.: US 11,951,184 B2
(45) Date of Patent: *Apr. 9, 2024

(54) VECTOR FOR GENE SILENCING AND REPLACEMENT AND METHODS OF USE THEREOF

(71) Applicant: WISCONSIN ALUMNI RESEARCH FOUNDATION, Madison, WI (US)

(72) Inventors: Matthew Michael Millette, Middleton, WI (US); Erik Wolfe Dent, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 129 days.

This patent is subject to a terminal disclaimer.

(21) Appl. No.: 17/346,639

(22) Filed: Jun. 14, 2021

(65) Prior Publication Data

US 2021/0316016 A1 Oct. 14, 2021

Related U.S. Application Data

(63) Continuation of application No. 16/257,615, filed on Jan. 25, 2019, now Pat. No. 11,071,791.

(60) Provisional application No. 62/622,479, filed on Jan. 26, 2018.

(51) Int. Cl.
| | | |
|---|---|---|
| C07H 21/04 | (2006.01) | |
| A61K 48/00 | (2006.01) | |
| A61P 25/28 | (2006.01) | |

(52) U.S. Cl.
CPC ...... *A61K 48/0066* (2013.01); *A61K 48/0008* (2013.01); *A61K 48/0058* (2013.01); *A61K 48/0091* (2013.01); *A61P 25/28* (2018.01)

(58) Field of Classification Search
None
See application file for complete search history.

(56) References Cited

U.S. PATENT DOCUMENTS

| | | |
|---|---|---|
| 2007/0044161 A1 | 2/2007 | Dickins et al. |
| 2019/0231899 A1 | 8/2019 | Millette et al. |

OTHER PUBLICATIONS

Babendure et al., "Control of Mammalian Translation by mRNA Structure Near Caps"; RNA; 12(5); pp. 851-861; (2006).
Bochkov et al.; "Translational Efficiency of EMCV IRES in Bicistronic Vectors is Dependent upon IRES Sequence and Gene Location"; BioTechniques; 41(3); pp. 283-292; (2006).

Chen et al.; "Modeling ALS with iPSCs Reveals that Mutant SOD1 Misregulates Neurofilament Balance in Motor Neurons"; Cell Stem Cell, 14, pp. 796-809, (2014).
Dent et al.; "GAP-43 Phosphorylation is Dynamically Regulated in Individual Growth Cones"; Journal of Neurobiology; 23(8); pp. 1037-1053; (1992).
Dent, Erik W., "Of Microtubules and Memory: Implications for Microtubule Dynamics in Dendrites and Spines"; Molecular Biology of the Cell, 28, pp. 1-8, (2017).
Fellmann et al.; "An Optimized MicroRNA Backbone for Effective Single-Copy RNAi"; Cell Reports; 5(6), pp. 1704-1713; (2013).
Fellmann et al.; "Functional Identification of Optimized RNAi Triggers Using a Massively Parallel Sensor Assay"; Molecular Cell; 41(6), pp. 733-746; (2011).
McVicker et al.; "Transport of a Kinesin-cargo Pair Along Microtubules into Dendritic Spines Undergoing Synaptic Plasticity"; Nat Commun. Sep. 23, 2016, 7:12741, 13 pages; online.
Merriam et al.; "Synaptic Regulation of Microtubule Dynamics in Dendritic Spines by Calcium, F-Actin, and Drebrin"; The Journal of Neuroscience; 33(42); pp. 16471-16482; (2013).
Mizui et al.; "Overexpression of Drebrin A in Immature Neurons Induces the Accumulation of F-actin and PSD-95 into Dendritic Filopodia, and the Formation of Large Abnormal Protrusions"; Mol. Cell. Neurosci.; 30(1); pp. 149-157; (2005).
Mizui et al.; "Drebrin E is Involved in the Regulation of Axonal Growth Through Actin-myosin Interactions"; 109(2); pp. 611-622; (2009).
Otey et al.; "B35 Neuroblastoma Cells: An Easily Transfected, Cultured Cell Model of Central Nervous System Neurons"; Methods in Cell Biology; 71; Chapter 13; pp. 287-303; 0091-679X/03; (2003).
Qin et al.; "Systematic Comparison of Constitutive Promoters and the Doxycycline-Inducible Promoter"; PLOS One, 5(5): e10611; 4 pages; (2010).
Schindelin et al.; "Fiji: an Open-source Platform for Biological-image Analysis"; Nature Methods; 9(7); pp. 676-682; (2012).
Viesselmann et al.; "Nucleofection and Primary Culture of Embryonic Mouse Hippocampal and Cortical Neurons"; Journal of Visualized Experiments; Issue 47, e2373, doi:10.3791/2373; pp. 1-4; (2011).

(Continued)

*Primary Examiner* — Kimberly Chong
(74) *Attorney, Agent, or Firm* — Karen A. LeCuyer; DeWitt LLP

(57) ABSTRACT

An expression cassette for gene silencing and replacement, including, in operable communication, a promoter, an expression attenuator, a nucleotide sequence encoding a gene for a replacement target protein, and an shRNA sequence for knockdown of an endogenous variant of the target protein, wherein the promoter, the expression attenuator, the nucleotide sequence encoding the gene for the replacement target protein, and the shRNA are expressed as a single transcript. Also included are expression vectors and cells. Also included are methods of silencing and replacement of a target gene in a cell in culture by transforming the cells with the expression vectors described herein. Also included are minimal expression cassettes suitable for therapeutic methods.

21 Claims, 7 Drawing Sheets

Specification includes a Sequence Listing.

(56) References Cited

OTHER PUBLICATIONS

Wu et al.; "Effect of Genome Size on AAV Vector Packaging"; Molecular Therapy; 18(1); pp. 80-86; (2010).
Barbosa, C. et al.; "Gene Expression Regulation by Upstream Open Reading Frames and Human Disease"; PLoS Genetics, vol. 9, Issue No. 8, e1003529; 2013; 12 pages; DOI:10.1371/journal.pgen.1003529.
Dvir, S. et al.; "Deciphering the rules by which 5'-UTR sequences affect protein expression in yeast"; PNAS, vol. 110, Issue No. 30; 2013; pp. E2792-E2801; DPO:10.1073/pnas.1222534110.
Ferreira, J. et al.; "Tuning gene expression with synthetic upstream open reading frames"; PNAS, vol. 110, Issue No. 28; 2013; pp. 11284-11289; DOI: 10.1073/pnas.1305590110.
Koh, E. et al.; "An Internal Ribosome Entry Site (IRES0 Mutant Library for Tuning Expression Level of Multiple Genes in Mammalian Cells"; PLoS One, vol. 8, Issue No. 12, e82100; 2013; 9 pages; DOI:10.1371/journal.pone.0082100.
Leppek, K. et al.; "Functional 5' UTR mRNA structures in eukaryotic translation regulation and how to find them"; Nature Reviews—Molecular Cell Biology, vol. 19, Issue No. 3; 2018; 17 pages; DOI:10.1038/nrm.2017.103.
Millette, M. et al.; "A Single Transcript Knockdown-Replacement Strategy Employing 5' UTR Secondary Structures to Precisely Titrate Rescue Protein Translation"; Frontiers in Genome Editing, vol. 4, Article 803375; 2022; 9 pgs.

SEQUENCE LISTING

<160> NUMBER OF SEQ ID NOS: 7

<210> SEQ ID NO 1
<211> LENGTH: 119

```
<212> TYPE: DNA
<213> ORGANISM: artificial
<220> FEATURE:
<223> OTHER INFORMATION: drebrin shRNA

<400> SEQUENCE: 1
aaggtatatt gctgttgaca gtgagcgacc cagaccagat tgtagcttat agtgaagcca      60
cagatgtata agctacaatc tggtctgggc tgcctactgc ctcggacttc aaggggcta     119

<210> SEQ ID NO 2
<211> LENGTH: 97
<212> TYPE: DNA
<213> ORGANISM: ARTIFICIAL
<220> FEATURE:
<223> OTHER INFORMATION: control shRNA

<400> SEQUENCE: 2
tgctgttgac agtgagcgca ctctttctag gaggttgtga tagtgaagcc acagatgtat      60
cacaacctcc tagaaagagt atgcctactg cctcgga                              97

<210> SEQ ID NO 3
<211> LENGTH: 97
<212> TYPE: DNA
<213> ORGANISM: ARTIFICIAL
<220> FEATURE:
<223> OTHER INFORMATION: EB3 97 shRNA #1

<400> SEQUENCE: 3
tgctgttgac agtgagcgct ttacaaagt cattggtata tagtgaagcc acagatgtat       60
ataccaatga ctttgtcaaa ttgcctactg cctcgga                              97

<210> SEQ ID NO 4
<211> LENGTH: 97
<212> TYPE: DNA
<213> ORGANISM: ARTIFICIAL
<220> FEATURE:
<223> OTHER INFORMATION: EB3 97 shRNA #1

<400> SEQUENCE: 4
tgctgttgac agtgagcgaa ctcaccaatt cttatttatt tagtgaagcc acagatgtaa      60
ataaataaga attggtgagt ctgcctactg cctcgga                              97

<210> SEQ ID NO 5
<211> LENGTH: 38
<212> TYPE: RNA
<213> ORGANISM: ARTIFICIAL
<220> FEATURE:
<223> OTHER INFORMATION: hairpin RNA

<400> SEQUENCE: 5
cggccgcaga cgccucuaua ucgaggcguc ugcggccg                              38

<210> SEQ ID NO 6
<211> LENGTH: 32
<212> TYPE: RNA
<213> ORGANISM: ARTIFICIAL
<220> FEATURE:
<223> OTHER INFORMATION: hairpin RNA

<400> SEQUENCE: 6
cggccgcaga cgcuauaucg cgucugcggc cg                                    32

<210> SEQ ID NO 7
```

```
<211> LENGTH: 26
<212> TYPE: RNA
<213> ORGANISM: ARTIFICIAL
<220> FEATURE:
<223> OTHER INFORMATION: hairpin RNA

<400> SEQUENCE: 7
cggccgcaga uauaucucug cggccg                                          26
```

VECTOR FOR GENE SILENCING AND REPLACEMENT AND METHODS OF USE THEREOF

CROSS-REFERENCE TO RELATED APPLICATIONS

This application is a continuation of U.S. application Ser. No. 16/257,615, filed on Jan. 25, 2019, which claims priority to U.S. Provisional Application 62/622,479 filed on Jan. 26, 2018, which is incorporated herein by reference in its entirety.

STATEMENT REGARDING FEDERALLY SPONSORED RESEARCH & DEVELOPMENT

This invention was made with government support under NS098372 and NS080928 awarded by the National Institutes of Health. The government has certain rights in the invention.

FIELD OF THE DISCLOSURE

The present disclosure is related to expression systems for gene silencing and replacement, and methods of using the expression systems, particularly in developmentally regulated proteins.

BACKGROUND

Interrogating the roles of individual proteins in complex biological processes requires the expression of functional mutants in both gain and loss of function experiments. However, background contribution of endogenous protein represents a primary confounding factor when interpreting the consequences of these alterations. This is particularly the case when proteins of interest are obligate dimers or multimers. One way researchers have attempted to overcome this dilemma is through direct gene editing via CRISPR-Cas9. While promising, genome editing is presently inefficient and commonly requires the generation of stable cell lines, an expensive and time consuming endeavor that requires significant investment in sequencing to ensure permanent off-target changes have not been introduced to the host genome. When applied to primary, post-mitotic cells, like neurons in culture, this approach becomes entirely impractical. Therefore, what is needed is a high-throughput, cost effective alternative which circumvents these caveats in first-line research applications.

BRIEF SUMMARY

In one aspect, an expression cassette for gene silencing and replacement of a target protein comprises, in operable communication,
a promoter,
an expression attenuator,
a nucleotide sequence encoding a gene for the replacement target protein, and
an shRNA sequence for knockdown of an endogenous variant of the target protein,
wherein the promoter, the expression attenuator, the nucleotide sequence encoding the gene for the replacement target protein, and the shRNA are expressed as a single transcript.

In another aspect, also included are expression vectors comprising the foregoing expression cassettes and cells comprising the expression vectors.

In yet another aspect, a method of silencing and replacement of a target gene in a cell in culture comprises transforming the cell with an expression vector as described herein, and optionally applying to the cell an inducer when the promoter is an inducible promoter to provide expression of the single transcript, wherein expression of the shRNA silences the expression of the endogenous variant of the target protein, and expression of the coding sequence for the replacement target protein provides the replacement target protein in the cell.

In another aspect, also included are expression vectors comprising the foregoing expression cassettes and cells comprising the expression vectors.

In yet another aspect, a therapeutic method comprises administering the foregoing expression vector, or transplanting the foregoing cell into a subject, such as a mammalian subject.

BRIEF DESCRIPTION OF THE DRAWINGS

(FIG. 2, Left) Immunostaining of neuronal cultures with drebrin antibody confirms effectiveness of RNAi. shRNA reporter-expressing cells are entirely depleted of drebrin, while adjacent non-transfected cell is revealed by robust anti-drebrin fluorescence. (FIG. 2, Right) Knockdown-Rescue with drebrin-GFP yields morphologically normal dendritic spines. Drebrin localizes expectedly and with specificity to dendritic spines.

Figure 1:
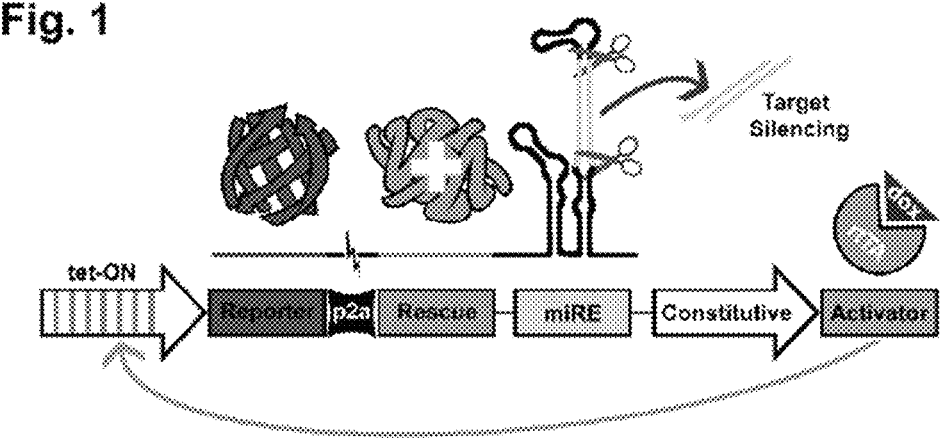
FIG. 1 shows an embodiment of an expression cassette. An expression cassette includes a tet-ON driven, single transcript design with an RFP-membrane reporter and rescue gene split by a P2A cleavage site to yield two separate proteins. RNAi is accomplished via the 3'UTR mir30 cassette, cleaved into shRNA targeting non-coding regions of endogenous gene of interest.

The above-described and other features will be appreciated and understood by those skilled in the art from the following detailed description, drawings, and appended claims.

DETAILED DESCRIPTION

Described herein are expression cassette-based knockdown/replacement (KDR) strategies to silence endogenous proteins and replace them with either a wild-type or functional mutant protein. The methodology can be adapted for in vitro (e.g., cell culture) and in vivo (e.g., therapeutic) applications. This methodology has a number of advantages: (1) KDR can be implemented quickly and inexpensively, without the need to create cell lines, thus it is especially useful in post-mitotic cells, such as neurons; (2) a total RNA knockdown/replacement strategy, e.g., miR-30-based, circumvents complications in gene editing like the presence of multiple alleles or large insertions; (3) KDR is useful for determining the function of different domains/sites within the protein of interest by expressing fluorescently-labeled mutant proteins in the absence of endogenous protein; (4) KDR can be used with an inducible system (e.g., a tet-inducible system) to turn on or off mutant protein replacement at a desired time, and functional reversal to baseline with inducer withdrawal; (5) the addition of tailored attenuating sequences at the RNA level will permit users to easily select desired expression levels; and (6) KDR could be implemented in translational medicine to knockdown endogenous mutant proteins and rescue them with a normal, functional version of the protein in patient-derived cell lines. This platform is of broad use to the cell biology community at large and provides novel treatment options for genetic disorders. Importantly, the demonstration of KDR in mature neurons, which are notoriously difficult to gene edit suggests that the methods described herein can be used in virtually any cell type.

The vectors and methods described herein can be implemented in the knockdown of mutant proteins and replacement with functioning wild-type proteins in an effort to "rescue" cells that normally express genetically mutant proteins. To accomplish this goal, the inventors have constructed several novel, self-contained, modular expression cassettes that employ a mir30 microRNA unit to knockdown endogenous protein, in conjunction with a rescue gene and fluorescent reporters to simultaneously implement a knockdown/replacement or knockdown/rescue strategy.

More specifically, the inventors have studied the contribution of cytoskeletal dynamics to synaptic plasticity. Specifically, the inventors are interested in how actin and microtubules (MTs) coordinate to direct the deposition of cargoes necessary for long-term potentiation (LTP) into synaptically active dendritic spines. In culture, as in vivo, neurons form dense and elaborate networks. Consequently, to directly visualize these processes, primary neurons must be transfected very sparsely. Through extensive comparison of available methods, the inventors determined that electroporation just prior to plating is the optimal means to achieve sparse transfection. Plasmid DNA must thus be tolerated for up to three weeks prior to imaging as neurons mature. Loss or gain of function experiments are critical for interrogating the functions of individual proteins in complex biological processes like learning and memory, but proteins of interest frequently serve critical roles in early neuronal development. Commonly employed paradigms overexpress or silence genes without acknowledging additional contributions outside the time-point of focus. Doing so risks, if not guarantees, aberrations in axon outgrowth, dendritic branching and spinogenesis. When development does not follow an entirely normal trajectory it is unfeasible to make functional comparisons in mature neurons.

The inventors developed the vectors and methods described herein to carry out complete, physiologically matched genetic replacement of proteins at specific developmental time points. An exemplary construct is shown in FIG. 1. The original design employs a current generation, tight doxycycline-inducible promoter and its corresponding transactivator (rTTA) gene downstream of a PGK promoter, which drives constitutive and uniform expression across many cell types. This permits the delay of expression of the construct by withholding doxycycline until neuronal maturity. The unique, single transcript approach incorporates a mir30 cassette in the 3'UTR of the rescue gene. This temporally locks endogenous gene silencing and replacement, and in contrast to most common shRNA delivery methods, functions downstream of any Pol II or III promoter. Further, a fluorescent cell membrane label and P2A peptide cleavage sequence flanks the rescue gene on its 5' side, permitting easy visual identification of induced cells. The efficacy of this strategy was confirmed using the actin-associated protein Drebrin (FIG. 2), which functions both in early neuronal development and postsynaptically. When Drebrin-GFP is over-expressed through development, it later contributes to actin accumulation and aberrant elongation of dendritic spines. No such morphological phenotype was observed when endogenous Drebrin was replaced with the same GFP tagged protein in adulthood, suggesting total levels remain within a physiologically relevant range.

Figure 3:
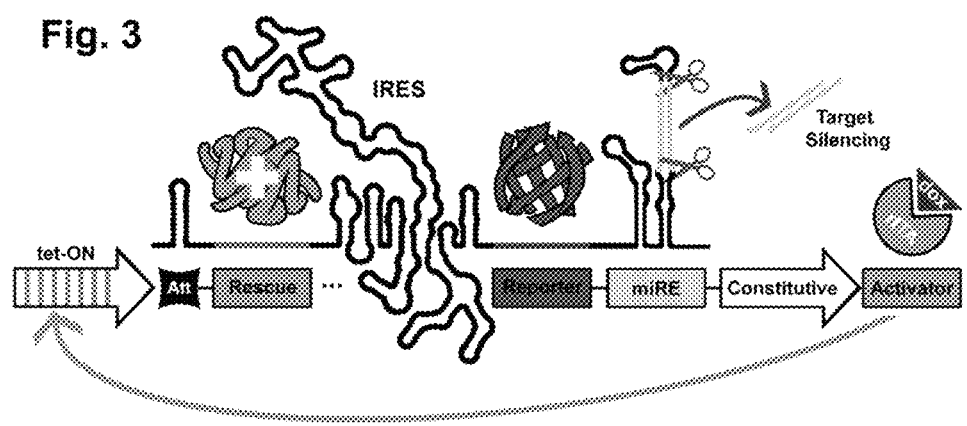
FIG. 3 shows an embodiment of an expression cassette. This design reorients the reporter downstream of an IRES element to provide a separate initiation site for translation. This maintains reporter brightness while allowing physiologically tunable attenuation of our rescue gene by interchanging 5'UTR hairpins.

While the construct of FIG. 1 achieves complete, timed replacement without inducing developmental abnormalities due to overexpression, Western blot analysis indicated that Drebrin-GFP levels were higher than endogenous levels. Without being held to theory, it was expected to match rescue gene expression to endogenous by titrating doxycycline induction. Additional modifications were made to improve on the original design in terms of translational control, ease of visualization and knockdown potency. (FIG. 3)

Because variable concentrations of doxycycline do not permit adequate control over rescue gene expression, 5'UTR hairpins were introduced before the initiation codon of the rescue gene because an inverse relationship between thermal stability of RNA secondary structure and translation efficiency has been shown. A range of 5'UTR sequences of varying thermal stability, e.g., between −10 kcal/mol and −50 kcal/mol, can be employed, and can be experimentally tuned to match endogenous expression.

A vector library can be created to permit end-user selection from pre-defined expression strength vectors that can then be matched to physiological levels of the protein of interest. In addition, the fluorescent membrane reporter can be located downstream of a native internal ribosomal entry site (IRES) from encephalomyocarditis virus (EMCV) to create two separate cistrons, rendering the 3' cistron unsusceptible to attenuation. Importantly, a large reduction in rescue protein translation permits maximal tet-ON promoter induction, greater total transcript number, and thus ensures maximal gene silencing potency and reporter brightness.

In an aspect, an expression cassette for gene silencing and replacement of a target protein comprises, in operable communication,
a promoter,
an expression attenuator,
a nucleotide sequence encoding a gene for the replacement target protein, and
an shRNA sequence for knockdown of an endogenous variant of the target protein,
wherein the inducible promoter, the expression attenuator, the nucleotide sequence encoding the gene for the replacement target protein and the shRNA are expressed as a single transcript.

The term "in operable communication" or "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "promoter" refers to a polynucleotide sequence capable of driving transcription of a coding sequence in a cell. The promoter can be a constitutive promoter or an inducible promoter. An "inducible promoter" is one that initiates transcription only under particular environmental conditions, developmental conditions, or drug or chemical conditions. For example, transcription of the single transcript is controlled by the presence of an inducer for the inducible promoter. Inducible promoters include Pol II and Pol III promoters. When the promoter is an inducible promoter, the transcription of the single transcript is controlled by the presence of an inducer for the inducible promoter In an aspect, the expression cassette further comprises a transactivator gene for the inducible promoter, wherein the transactivator gene for the inducible promoter is operably linked to a constitutive promoter.

An exemplary inducible promoter is the tight doxycycline-inducible promoter and its corresponding transactivator (rTTA) gene. In this embodiment, the expression cassette further comprises a transactivator gene for the inducible promoter, wherein the transactivator gene for the inducible promoter is operably linked to a constitutive promoter. In an embodiment, the inducible promoter is a tetracycline-responsive promoter. The tetracycline-responsive promoter can be activated at the presence of tetracycline (tet), doxycycline (Dox), or a tet analog.

An alternative inducible promoter is a lac operator system. Briefly, a Lac operator sequence (LacO) is inserted into the promoter region. The LacO is preferably inserted between the PSE and the transcription initiation site, upstream or downstream of the TATA box. In some embodiments, the LacO is immediately adjacent to the TATA box. The expression of the cassette is thus under the control of IPTG (or any analogue thereof). Addition of IPTG relieves repression of the promoter by a Lac repressor (i.e., the LacI protein) that the host cells are also engineered to express. Since the Lac repressor is derived from bacteria, its coding sequence may be optionally modified to adapt to the codon usage by mammalian transcriptional systems and to prevent methylation.

Additional inducible systems include a LoxP-stop-LoxP system in which expression is induced by addition of Cre recombinases. The "Stop" sequences in the cassette prevent the RNA polymerase III from extending an RNA transcript beyond the cassette. Upon introduction of a Cre recombinase, however, the LoxP sites in the cassette recombine, removing the Stop sequences and leaving a single LoxP site. Removal of the Stop sequences allows transcription to proceed through the hairpin sequence, producing a transcript that can be efficiently processed into an open-ended, interfering dsRNA.

Expression attenuators are RNA elements that can modulate translation efficiency. In an embodiment, an expression attenuator comprises one or more 5' UTR sequences that form hairpins with thermal stabilities of, for example, −10 to −50 kcal/mol, which inhibits translation through steric hindrance of the ribonuclear initiation complex in accessing the rescue gene initiation codon. The number and/or stability of 5' UTR hairpins tunes the level of translation of the replacement target protein. In addition to hairpins, examples of other 5'UTR elements which inhibit protein translation include, but are not limited to, secondary and tertiary structures of pseudoknots, stem-loops, viral or cellular internal ribosomal entry sites (IRES), RNA G-quadruplexes (RG4s), upstream open reading frames (uORFs), upstream start codons (uAUGs), lncRNA associating sequences, and sequences recruiting inhibitory proteins, for example, iron response element (IRE). In an embodiment, the expression cassette comprises an operably linked IRES upstream of a reporter gene.

The expression cassette includes a nucleotide sequence encoding a gene for a replacement target protein. The term "nucleotide sequence encoding a gene" means a nucleic acid sequence comprising the coding region of a gene or in other words the nucleic acid sequence, which encodes a gene product, e.g., a protein. The coding region may be present in either a cDNA, genomic DNA or RNA form.

The terms "nucleic acid molecule encoding", "DNA sequence encoding", and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "gene" means the deoxyribonucleotide sequences comprising the coding region of a gene, e.g., a structural gene, and optionally including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The expression cassette also includes a shRNA sequence for knockdown of an endogenous variant of the target protein. A short hairpin RNA or small hairpin RNA (shRNAllairpin Vector) is an artificial RNA molecule with a tight hairpin turn that can be used to silence target gene expression via RNA interference (RNAi). In an embodiment, the shRNA is on the form of a precursor molecule comprising the sequence of the shRNA and a microRNA (miR) such as miR-30. Such constructs are described in US20070044164, incorporated by reference herein. The precursor molecule is processed in the cell to provide the shRNA which can then silence the endogenous target gene.

Exemplary target genes include target genes that encode developmentally regulated proteins or proteins wherein expression of the protein interferes with normal cell division. Because the target gene would be inactive until induction, the cells could proliferate normally until induction. The expression cassettes thus allow for study of proteins that are normally difficult to study such as developmentally regulated proteins and cell cycle proteins. For example, cell-cycle proteins include cyclin-dependent kinases, mitogen-activated kinases, cyclins, phosphoprotein phosphatases and their substrates such as chromatin-associated proteins, cytoskeletal proteins, and transcription factors.

Exemplary target genes include target genes that encode a developmentally regulated protein, e.g., a protein whose quantity or function changes during specific developmental stages. Exemplary proteins which function in neuronal development include EB1, EB3, drebrin, Cdk5, NMDA receptor subunits, AMPA receptor subunits, and the like.

In an embodiment, the expression cassette further comprises an operably linked IRES upstream of a reporter gene, e.g., a gene encoding a luciferase, a fluorescent protein (e.g., GFP, RFP, YFP, BFP, etc.), or an enzyme, or any other art-recognized reporter whose physical presence and/or activity can be readily assessed using an art-recognized method. The IRES sequence directs expression of the reporter gene.

In an aspect, a method of silencing and replacement of a target gene in a cell in culture, comprises
  transforming the cell with an expression vector comprising an expression cassette as described above, and
  optionally applying to the cell an inducer when the promoter is an inducible promoter to provide expression of the single transcript, wherein expression of the shRNA silences the expression of the endogenous variant of the target protein, and expression of the coding sequence for the replacement target protein provides the replacement target protein in the cell.

Exemplary cells include a primary neuronal cell, an astrocyte, an oligodendrocyte, or a cardiomyocyte. In this aspect, the transforming may be done one or more weeks prior to applying the inducer, specifically two or three weeks prior to applying the inducer.

Figure 4:
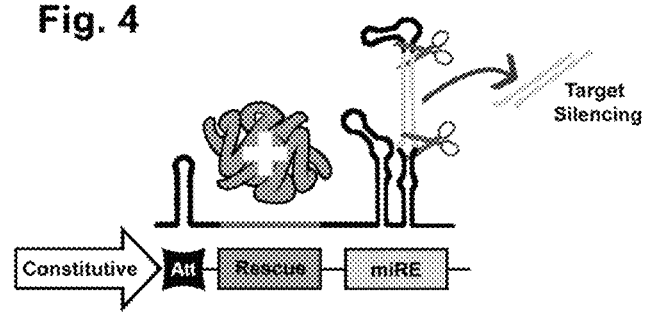
FIG. 4 is an embodiment of a "minimal" expression cassette lacking the IRES and reporter for applications where viral packaging capacity is limited and is designed to be easily transferable between vectors.

For very large genes where viral packaging limitations are of concern, the minimal version of the expression cassette shown in FIG. 4 can be used. This minimal version of the expression cassette was designed with portability in mind to function as a vector agnostic, physiologically tunable gene therapy construct.

In an aspect, an expression cassette for gene silencing and replacement comprises, in operable communication, a constitutive promoter, an expression attenuator, a nucleotide sequence encoding a gene for a replacement target protein, and an shRNA sequence for knockdown of an endogenous variant of the target protein, wherein the constitutive promoter, the expression attenuator, the coding sequence and the shRNA are expressed as a single transcript.

Constitutive promoters initiate mRNA synthesis independent of the influence of regulation. Exemplary mammalian constitutive promoters include the human β-actin (ACTB) promoter, the SV40 promoter, the cytomegalovirus (CMV) promoter, the ubiquitinC (UBC) promoter, the elongation factor-1α (EF1A) promoter, the phosphoglycerate kinase (PGK) promoter, and the CAGG composite promoter.

The expression attenuator, the coding sequence and the shRNA are as described above.

Also included herein are expression vectors comprising the expression cassettes described herein. As used herein, the term "expression vector" means a recombinant DNA molecule containing a desired coding sequence and appropriate nucleic acid sequences necessary for the expression of the operably linked coding sequence in a particular host organism. Expression vectors include high and medium copy number plasmids as known in the art.

Exemplary vectors include plasmids, phagemids, viruses, or vehicles derived from viral or bacterial sources that have been manipulated by the insertion or incorporation of the expression cassettes described herein, and free nucleic acid fragments which can be attached to these nucleic acid sequences. Viral and retroviral vectors include nucleic acid sequences from Moloney murine leukemia virus, Murine stem cell virus, Harvey murine sarcoma virus, murine mammary tumor virus, Rous sarcoma virus, adenovirus, adeno-associated virus, SV40-type viruses, polyoma viruses, Epstein-Barr viruses, papilloma viruses, herpes viruses, vaccinia viruses, polio viruses, lentiviruses, and RNA viruses such as retroviruses.

The term "transformation" as used herein refers to the introduction of foreign DNA into cells. Cells can thus be transformed with the expression vectors described herein. Transforming includes liposome fusion (transposomes), transfection, infection by viral vectors, and routine nucleic acid transfection methods such as electroporation, calcium phosphate precipitation and microinjection. In some embodiments, the vectors are integrated into the genome of a transgenic animal (e.g., a mouse, a rabbit, a hamster, or a nonhuman primate).

Further included are cells comprising the expression cassettes and expression vectors described herein, e.g., a cell transformed with an expression vector. Host cells include eukaryotic cells, e.g., dendritic cells, CHO cells, COS cells, yeast expression systems and recombinant baculovirus expression in insect cells, etc. Exemplary cells include primary neuronal cells, astrocytes, oligodendrocytes, and cardiomyocytes. Exemplary cell lines include B35 rat neuroblastoma cells, Cos 7 monkey kidney cells, HEK human embryonic kidney cells, CAD mouse Cath.a-differentiated catecholaminergic neuron-like cells, PC12 rat pheochromocytoma neuron-like cells, and the like.

An "ex vivo" method as used herein is a method which involves isolation of a cell from a subject, manipulation of the cell outside of the body, and reimplantation of the manipulated cell into the subject. The ex vivo procedure may be used on autologous or heterologous cells but is preferably used on autologous cells.

A therapeutic method comprises administering the expression vector, or transplanting a cell as described herein into a subject in need thereof, such as a mammalian subject, specifically a human subject. Exemplary subjects are suffering from Amyotrophic Lateral Sclerosis Disease, Leukodystrophy Disease, Alzheimer's Disease, Parkinson's Disease and the like.

The invention is further illustrated by the following non-limiting examples.

EXAMPLES

Methods

Plasmid Construction: The pmAtt plasmid (FIG. 3) was constructed using the ampicillin promoter, ampicillin resistance gene, SV40 polyadenylation sequence, SV40 origin of replication, SV40 promoter, CAP binding site, lac promoter, lac operator, and beta-globin polyadenylation sequence from the widely used pCAX expression vector. Standard molecular cloning practices including DNA digestion by restriction enzyme, DNA ligation, gene splicing by overlap extension, isothermal assembly, and Gibson assembly were used to join the following sequences, in order from 5' to 3': tet-inducible promoter, Attenuator Sequence, Multiple Cloning Site comprised of AatII, SbfI, NheI, SalI, and NotI recognition sequences, mScarlet-I, EMCV IRES, fluorescent reporter protein pmiRFP670, enhanced mIR30 cassette, human PGK promoter, and reverse tetracycline transactivator. The resulting product was joined with the above-mentioned pCAX-sourced elements for bacterial expression and replication to complete the "pmAtt" gene knockdown/rescue vector. The constitutively expressed version was generated by the same molecular techniques but instead joined the ubiquitously expressed EF1a promoter backbone, with the multiple cloning sites, EMCV IRES, mScarlet-I, and miR30 cassette.

Sources of DNA
a.) tet-inducible promoter was sourced from Addgene plasmid #41393
b.) Attenuator hairpins and Multiple Cloning Site were ordered as oligos from IDT
c.) mScarlet-I was ordered from IDT as a codon optimized geneblock based on reference Addgene plasmid #79987
d.) EMCV IRES was sourced from Addgene Plasmid #27296
e.) Fluorescent reporter protein pmiRFP670 was ordered from IDT as a codon optimized geneblock based on reference Addgene plasmid #79987
f) miR30 cassette was sourced from Addgene plasmid #73576
g.) Human PGK promoter was sourced from Addgene plasmid #41393
h.) Reverse tetracycline transactivator was sourced from Addgene plasmid #41393
i.) shRNA target sequences were ordered from IDT as ultramers
j.) The EF1a promoter was sourced from Addgene plasmid #11154 shRNA Design: Target sites for RNA interference were chosen using the Cold Spring Harbor RNAi utility. Targets in the 3'UTR were given preference to avoid needing to introduce silent mutations to rescue genes to render them insensitive. shRNA-coding 97 nucleotide ultramers were ordered from IDT, amplified by PCR and cloned into the miR30 cassette by restriction digest with XhoI and EcoRI, and subsequent ligation.

The drebrin 97-mer sequence is as follows:

(SEQ ID NO: 1)
5'-AAGGTATATTGCTGTTGACAGTGAGCGACCCAGACCAGATTGTAGC
TTATAGTGAAGCCACAGATGTATAAGCTACAATCTGGTCTGGGCTGCCT
ACTGCCTCGGACTTCAAGGGGCTA-3'

Control, mammalian non-targeting 97-mer sequence based on C. elegans target MIMAT0000039 is as follows:
(SEQ ID NO: 2)
5'-TGCTGTTGACAGTGAGCGcACTCTTTCTAGGAGGTTGTGATAGTGA
AGCCACAGATGTATCACAACCTCCTAGAAAGAGTATGCCTACTGCCTCG
GA-3'

EB3 97-mer sequence #1 is as follows:
(SEQ ID NO: 3)
5'-TGCTGTTGACAGTGAGCGCTTTGACAAAGTCATTGGTATATAGTGA
AGCCACAGATGTATATACCAATGACTTTGTCAAATTGCCTACTGCCTCG
GA-3'

EB3 97-mer sequence #2 is as follows:
(SEQ ID NO: 4)
5'-TGCTGTTGACAGTGAGCGAACTCACCAATTCTTATTTATTTAGTGA
AGCCACAGATGTAAATAAATAAGAATTGGTGAGTCTGCCTACTGCCTCG
GA-3'

Attenuator Sequences: Novel hairpin sequences of graded stability were generated referencing work published in Babendure and colleagues (Babendure et al., 2006). mRNA secondary structures were modeled using the State University of New York at Albany RNA Institute's "mfold" web server. This DNA was ordered from IDT as single stranded ultramers and cloned into AatII and NolI digested vector using NEB HIFI assembly mix using manufacturer-recommended protocol.

Cell Culture and Transfections: Primary hippocampal neurons were prepared from Sprague Dawley rats (Harlan) at E18.5 (McVicker D P, Awe A M, Richters K E, et al. Transport of a kinesin-cargo pair along microtubules into dendritic spines undergoing synaptic plasticity. Nat Commun. 2016; 7:12741). Briefly, rat hippocampi were dissected, trypsinized and transfected with plasmid DNA while in suspension using the Amaxa Nucleofector™, per manufacturer instructions. Neurons were plated at a density of $30 \times 10^3$ neurons per cm$^2$ on 0.001 mg ml-1 PEI (Sigma)-coated coverslips, which were adhered to 35 mm plastic culture dishes containing a 15 mm hole drilled through the chamber. Neurons were plated with plating media (PM; neurobasal media with 5% fetal bovine serum (FBS), B27 supplement, 2 mM glutamine, 0.3% glucose and 37.5 mM NaCl) for 1 h at 5.0% $CO^2$ and 37° C. after which the chambers were flooded with 2 ml of serum-free media (PM with no added FBS). For tet-ON promoter induction 1 ug/uL doxycycline was maintained in culture media. All procedures were approved by the University of Wisconsin Committee on Animal Care and were in accordance with the NIH guidelines. For attenuator potency measurements, B35 cells were plated at a density of 10×103 cells per cm2 on 0.001 mg ml-1 PEI (Sigma)-coated coverslips in chambers as described for neuronal cultures. 24 hours after plating B35 cells were transfected with experimental constructs using Lipofectamine transfection reagent (Thermo Fisher Scientific) according to supplier's protocol.

Immunocytochemistry: Neurons were fixed in 4% paraformaldehyde-KREB-sucrose at 37° C. (Dent and Meiri, 1992), rinsed in PBS, blocked with 10% BSA and permeabilized in 0.2% Triton X-100. Neurons were incubated for 1 h at room temperature with primary rabbit anti-Drebrin antibody (1:500 Abcam ab60933), followed by a 1 h incubation with the secondary goat anti-rabbit alexa-568-conjugated antibodies (1:500; Life Technologies).

Microscopy, Image Processing and Analysis: Time-lapse images of live cultures were acquired either on a Nikon TE2000E microscope with total internal reflection fluorescence (TIRF) illuminator (Nikon) and Evolve EMCCD camera (Photometrics) with 100×/1.4 NA objective or a Zeiss LSM800 scanning confocal system with 63×/1.4 NA objective. During time-lapse microscopy, neurons were kept at 37° C. in a chamber enclosing the microscope. The imaging chamber was fitted with a glass ring and sealed with silicone grease and a glass coverslip to maintain appropriate CO2 levels. Time-lapse images were acquired every 5 seconds and spanned 10 minutes per neuron. All image processing and quantification was carried out in Fiji (Schindelin et al., 2012). Depending on experimental parameters MTs were visualized by fluorescent tubulin, EB1 or EB3. Secondary and tertiary branches of hippocampal pyramidal cells were selected preferentially. Invasions were manually quantified by frame-by-frame scrutiny of time-lapse images and supported by kymographs. The percentage of spines invaded was determined by dividing the number of invaded spines over the imaging period by the total number of spines in the dendritic field. Invasion frequency was defined by the total number of invasions divided by the number of spines invaded. For immunofluorescence analysis, image stacks of fixed neurons were acquired using a 63× objective on a Zeiss scanning confocal. For attenuator strength measurements B35 cells were imaged with a 20× objective on a Zeiss scanning confocal. ROIs were drawn over individual cell bodies such that GFP fluorescence downstream of the attenuator could be ratioed to RFP housekeeper for internal control on a cell-by-cell basis.

Graphing and Statistics: Graphpad Prism was used for all graphing and statistical analyses. For all data comparing more than two conditions, a one-way analysis of variance and Tukey's post hoc tests were performed. For data comparing only two conditions, a Student's t-test was performed. Data with P values less than 0.05 were considered statistically significant. On all graphs *P<0.05, P<0.01 and *P<0.001, ****P<0.0001. Cells analyzed were collected from a minimum of three preparations.

Example 1: Knockdown and Rescue of Drebrin

Figure 2:
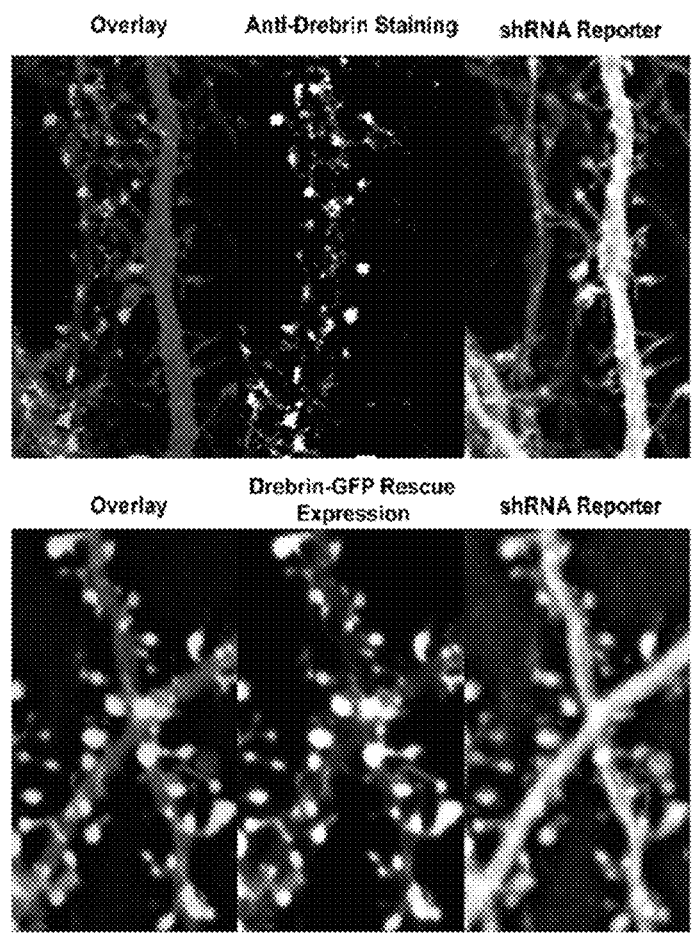
FIG. 2 shows the results of knockdown-rescue with Drebrin-GFP induced in DIV21 rat hippocampal neurons yields morphologically normal dendritic spines. Hippocampal cultures were transfected with plasmid encoding either drebrin-targeting shRNA and no rescue gene, or drebrin-GFP rescue gene and drebrin-targeting shRNA. Cultures were allowed to mature for 14 days prior to tet-ON promoter induction with doxycycline. Cultures were fixed at 21 days, and shRNA-only dishes were immunostained with anti-drebrin antibody.

A construct according to FIG. 1 was created and the data is shown in FIG. 2. Hippocampal cultures were transfected with plasmid encoding either drebrin-targeting shRNA and no rescue gene, or drebrin-GFP rescue gene and drebrin-targeting shRNA. Cultures were allowed to mature for 14 days prior to tet-ON promoter induction with doxycycline. Cultures were fixed at 21 days, and shRNA-only dishes were immunostained with anti-drebrin antibody. Full procedural details documented in materials and methods. (FIG. 2, Left) Immunostaining of neuronal cultures with drebrin antibody confirms effectiveness of RNAi. shRNA reporter-expressing cells are entirely depleted of drebrin, while adjacent non-transfected cell is revealed by robust anti-drebrin fluorescence. (FIG. 2, Right) Knockdown-Rescue with drebrin-GFP yields morphologically normal dendritic spines. Drebrin localizes expectedly and with specificity to dendritic spines.

Example 2: Knockdown-Rescue Technology in an Amyotrophic Lateral Sclerosis Disease Model Amyotrophic Lateral Sclerosis (ALS), also known as Lou Gehrig's disease, is the most common adult motor neuron disease. The hallmark of ALS is the selective dysfunction and death of the neurons that control muscle movement. ALS has no known cure, though experimental treatments are aimed to ameliorate symptoms and extend life. Approximately 90% of ALS diagnoses are linked to mutations in the SOD1 gene. SOD1 is a cytoplasmic, antioxidant enzyme which serves as the first step in superoxide radical metabolism. Over 150 different SOD1 mutations have been identified in humans. However, the Ala4Val (A4V) point mutation is present in approximately 50% of American ALS patients, while the Asp90Ala (D90A) is present in the majority of European cases. Virtually all SOD1 mutations act in a dominant manner, requiring only one mutated copy of the gene for disease manifestation, and under cellular stress even wild-type SOD1 can contribute to pathology. It is suspected, but not mechanistically understood how, mutations in SOD1 result in toxic gain-of-function, promoting the formation of protein aggregates which ultimately underlie ALS pathology. A knockdown/rescue construct according to the present disclosure will be used to halt and reverse disease progression in patient-derived SOD1 A4V and D90A mutant iPSCs.

Patient-derived in vitro models are appreciated to recapitulate pathologic phenotypes, even in young, developing cells. These iPSCs can be cultured and differentiated into distinct neuronal subtypes to study the pathophysiology of sporadic or familial forms of ALS. These in vitro models offer the advantage that the test system accurately represents human disease and provides a platform for testing new interventions for direct translation to clinical trials. Mutant SOD1 no longer performs its canonical function but may also contribute to oxidative stress through accumulation in mitochondrial membranes. However, the ways which misfolded SOD1 contributes to pathology are many and varied. SOD1 D90A promotes neurofilament (NF) aggregation by binding to the 3'UTR the long NF isoform RNA and decreases its stability. The resulting imbalance between isoforms leads to accumulation of neurofilament aggregates in cell bodies and axons. It is also increasingly evident that MTs are a critical component of ALS pathology. Misfolding of mutant SOD1 permits it to interact with tubulin directly, and with the anterograde motor protein kinesin-2 complex via kinesin-associated protein 3 (KAP3), as well as the dynein-dynactin retrograde motor complex.

Experimental Design: Control and SOD1 A4V (ND35671) and D90A (ND35660) iPSCs will be procured from the NINDS Human Cell and Data Repository. iPSCs will be transfected with necessary constructs at plating using the Amaxa Nucleofector™ system. Cell pellets will be collected at DIV 7 and 14 for undifferentiated iPSCs, and we will also transfect and plate differentiated motor neuron-like neurons for biochemical readout and confocal imaging. It is predicted that the SOD1 KDR construct will A) clear mutant SOD1 and replace with wild-type, and B) restore normal morphology and function in neurons.

Clear toxic SOD1 from iPSCs/neurons: Protein extracts will be made from cell pellets. A simple readout using Western blot to probe for SOD1 levels will be used. However, primary antibodies will have affinity for both mutant protein and wild-type rescue protein. It is expected to achieve complete depletion of mutant SOD1, but for clarity in this experiment only GFP-SOD1 will be expressed, which will result in a 27 kDa shift in molecular weight and appear as a distinct band. Cells will be fixed and stained for immunocytochemistry to quantify SOD1 aggregates via microscopy.

Analyze morphology of iPSC-derived motor neurons. SOD1 mutants have characteristic axonal beading. As a general marker of neuronal health, cultures will be imaged at 10 DIV with DIC microscopy to analyze whether this phenotype is restored following SOD1 KDR. Beading will be defined as enlargements of the neurite at least twice its local diameter (Chen H, Qian K, Du Z, et al. Modeling ALS with iPSCs reveals that mutant SOD1 misregulates neurofilament balance in motor neurons. Cell Stem Cell. 2014; 14(6): 796-809).

Label and quantify neurofilament aggregates. 10 DIV cultures will be stained and imaged with antibodies recognizing NF protein to determine if the intensity of staining is reduced by SOD1 KDR. Aggregates will be defined as focal accumulations with 3-fold higher intensity of NF label (Chen et al., 2014).

Label and measure mitochondria. SOD1 aggregates are often present in the mitochondrial intermembrane space, which is thought to cause mitochondrial swelling and vacuole formation. MitoTracker® Green (ThermoFisher) will be used to label and visualize mitochondria. Confocal microscopy will be used to acquire 63× magnification image stacks and compare the volume of untreated SOD1 A4V and D90A cells to KDR cells to determine if treatment eliminates this phenotype.

Analyze multiple metrics of axonal transport. Protein aggregates may disrupt axonal transportation, resulting in retraction of axonal terminals and denervation of muscles before the loss of cell bodies. Kinesin and dynein movement of expressed GFP-tagged constructs will be tracked, and the anterograde and retrograde transport of membrane-bounded vesicles and organelles will be tracked. Kymographs will be drawn over neurites and number, velocity and pausing of these individual puncta will be compared between untreated SOD1 A4V and D90A cells to KDR cells to determine if treatment eliminates this phenotype.

Example 3: Knockdown-Rescue in a Leukodystrophy Disease Model

Myelin plays a fundamental role in axon function and maintenance and its failure to develop normally in the leukodystrophies or its loss leading to demyelination, results in severe clinical dysfunction. The leukodystrophies are genetic disorders of white matter, primarily affecting the CNS. Advances in the understanding of the pathophysiology of the leukodystrophies will help guide the development of therapeutic strategies and have been hugely helped by animal models, either spontaneous mutants or those generated using transgenic or other contemporary techniques. The overarching goal is to utilize a new and exciting finding in an established myelin mutant, the taiep rat, that defines it as a model for the leukodystrophy caused by mutations in the TUBB4A gene. In both the human and rat disease, point mutations of the TUBB4A gene (A302T) result in microtubule (MT) accumulation in oligodendrocytes (OLs) which leads to their dysfunction. These experiments will define how the taiep mutation disrupts MT dynamics in OLs in culture. This defect will be corrected in mutant cells by simultaneously knocking down the point mutant TUBB4A gene and rescuing expression with a wild type (WT) TUBB4A gene in cultured OLs. To confirm that the TUBB4A mutation is the cause of the myelin defect and test that replacement of the point mutant TUBB4A with a normal TUBB4A gene creates functional repair, we will determine whether the knockdown/replaced OLs can myelinate axons following transplantation into a myelin deficient environment.

The hypothesis that MT accumulation in taiep rat OLs results from changes in MT dynamics will be tested. To test this hypothesis, MT polymerization/depolymerization kinetics will be monitored in OLs in tissue culture. A knockdown/rescue strategy as described herein will be used to determine if MT kinetic defects and MT accumulation can be reversed in taiep rat OLs in culture.

Expected Results and Interpretation: MT dynamics will be imaged with fluorescently-tagged EB3 or tubulin. It is predicted that the MTs in the taiep OLs will be more stable, spending more time in a paused state, polymerize and depolymerize at slower rates and over shorter distances. It is also predicted that the taiep OLs will produce accumulations of MTs in tightly packed arrays, while the WT OLs will not. The presence or absence of these tightly packed MT arrays will be imaged in cultured OLs with STED microscopy after labeling with antibodies to tubulin, obviating the need to use transmission EM, which is the standard methodology for imaging individual MTs in cells.

In the second set of experiments, it is predicted that the expression of the knockdown/rescue construct (knockdown of taiep Tubb4a A302T mutant and replacement with WT Tubb4a) will revert the MT dynamics observed in the taiep OLs into WT MT dynamics and inhibit the accumulation of MTs. Conversely, it is predicted that in WT OLs the knockdown of WT Tubb4a and replacement with the taiep Tubb4a A302T mutant will induce MT dynamic defects and cause the accumulation of MTs, as is seen in taiep OLs. Together, these experiments will determine if the Tubb4a A302T mutant is both necessary and sufficient for defects in MT dynamics and accumulation of MTs in OLs. It is predicted that that other human Tubb4a mutants (N414K and D249N) will cause changes in MT dynamics similar to the taiep Tubb4a A302T mutation and may also lead to MT accumulation in OLs.

The hypothesis that the Tubb4a mutation is the causative defect and that correction of the genetic defect in taiep OLs will result in their ability to myelinate axons normally in vivo will also be tested. To test this hypothesis, corrected cells will be transplanted into the spinal cord of the myelin deficient rat and the taiep rat and it will be determined whether the differentiating OLs do not accumulate MTs and ensheath and myelinate axons.

Expected Results and Interpretation: The primary goal is to test whether corrected OLs do not develop accumulation of MTs as seen in vivo in the taiep rat and are able to myelinate axons normally. Definitive evidence of this will confirm that indeed the mutation in the Tubb4a gene is causative.

The myelin deficient (md) rat has practically no myelin thus it will be used as a first test of the myelinating capacity of the transplanted cells. As such, myelin made by transplanted cells will be obvious. The thickness of myelin will be confirmed using the g ratio in all three transplant groups expecting the non-corrected taiep cells to produce only thin myelin sheaths. In the transplanted taiep rat, cells will be located in GFP-positive areas. In adjacent sections embedded in plastic, areas corresponding to the GFP-positive areas, will be examined for evidence of patches of myelin where the myelin sheaths are thicker than adjacent areas where axons are myelinated but hypomyelinated. Confirmation that this myelin is normal will be derived from g ratio measurements of myelinated fibers in the transplant compared to adjacent areas where the g ratios will be greater. Transplanting into the fasciculus gracilus of 3 month old taiep rats will test the ability of the corrected cells to myelinate demyelinated axons that are progressively found from 3 months on, compared to transplanting at 7 days where axons are waiting to be myelinated for the first time.

EM will be used to determine whether the corrected/transplanted cells do not develop an excess of MTs. From observations on the 8-12 day old taiep rat optic nerve, it is expected that MT accumulation begins in vivo as soon as OLs ensheath and myelinate axons. There is a clear increase of MTs in the cytosol and OL processes as well as their alignment along smooth and rough ER. Thus, it is predicted that, though not quantitative, distinction between 'corrected' and uncorrected OLs will be straightforward in these transplant experiments. In addition, as well as the comparison of endogenous vs. transplanted cells, these results can be compared with those from the control experiments, i.e., WT cells into mutant and taiep cells into mutant. In these experiments, WT cells should myelinate normally with normal OLs. Taiep cells will hypomyelinate axons and OLs will have accumulation of MTs. As the transplanted taiep rats can be followed for longer than the md rats, MT accumulation can be evaluated and should it develop later and in contrast whether the 'corrected' phenotype, i.e. normal MT number persists. The ability to follow the transplanted corrected cells for longer periods of time in the taiep recipient may be required for myelin made by these cells to reach a normal g ratio. Hence using both mutant rats as recipients will be beneficial and complimentary.

Example 4: Knockdown and Replacement of EB3 with Mutant Protein

Figure 5:
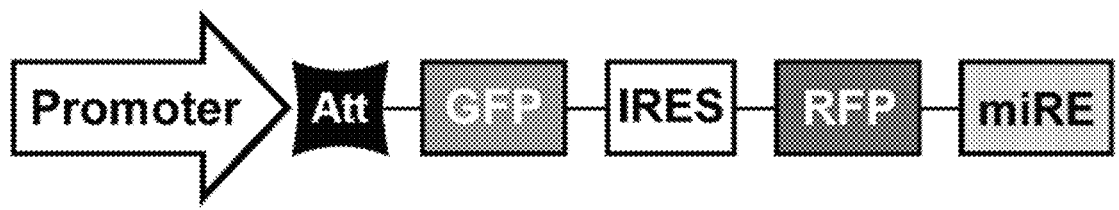
FIG. 5 is a diagram of the vector used to determine potency of hairpin structures under physiologically relevant, live-cell conditions.

FIG. 5 is a diagram of the vector used to determine potency of hairpin structures under physiologically relevant, live-cell conditions. In this instance a green fluorescent protein (GFP) gene has been cloned into the "rescue" gene position and is ratioed to a red fluorescent protein (RFP) "housekeeper" produced from a functionally separate IRES initiation site, which is unimpacted by attenuation.

Figure 6:
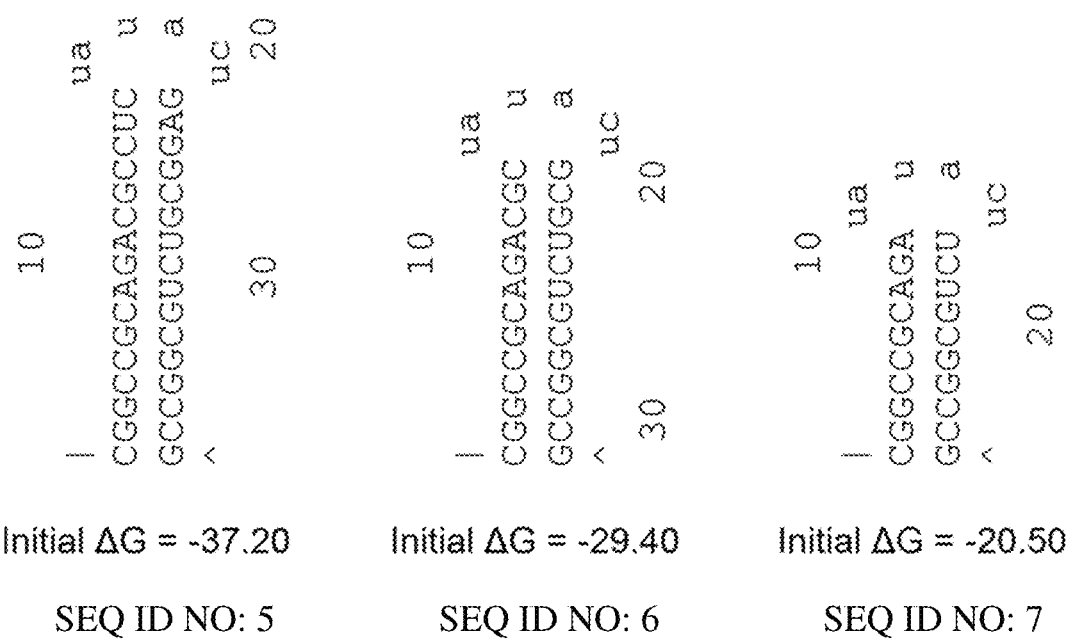
FIG. 6 shows examples of graded-stability hairpins used to diminish protein translation of "rescue" genes.

FIG. 6 shows examples of graded-stability hairpins used to diminish protein translation of "rescue" genes. Thermal stability is reduced step-wise by sequential removal of nucleotide base-pairs immediately adjacent to loop, which keeps the remaining sequence otherwise consistent.

```
Hairpin 1:
                                    (SEQ ID NO: 5)
CGGCCGCAGACGCCUCUAUAUCGAGGCGUCUGCGGCCG Hairpin 2:
                                    (SEQ ID NO: 6)
CGGCCGCAGACGCUAUAUCGCGUCUGCGGCCG Hairpin 3:
                                    (SEQ ID NO: 7)
CGGCCGCAGAUAUAUCUCUGCGGCCG
```

Figure 7:
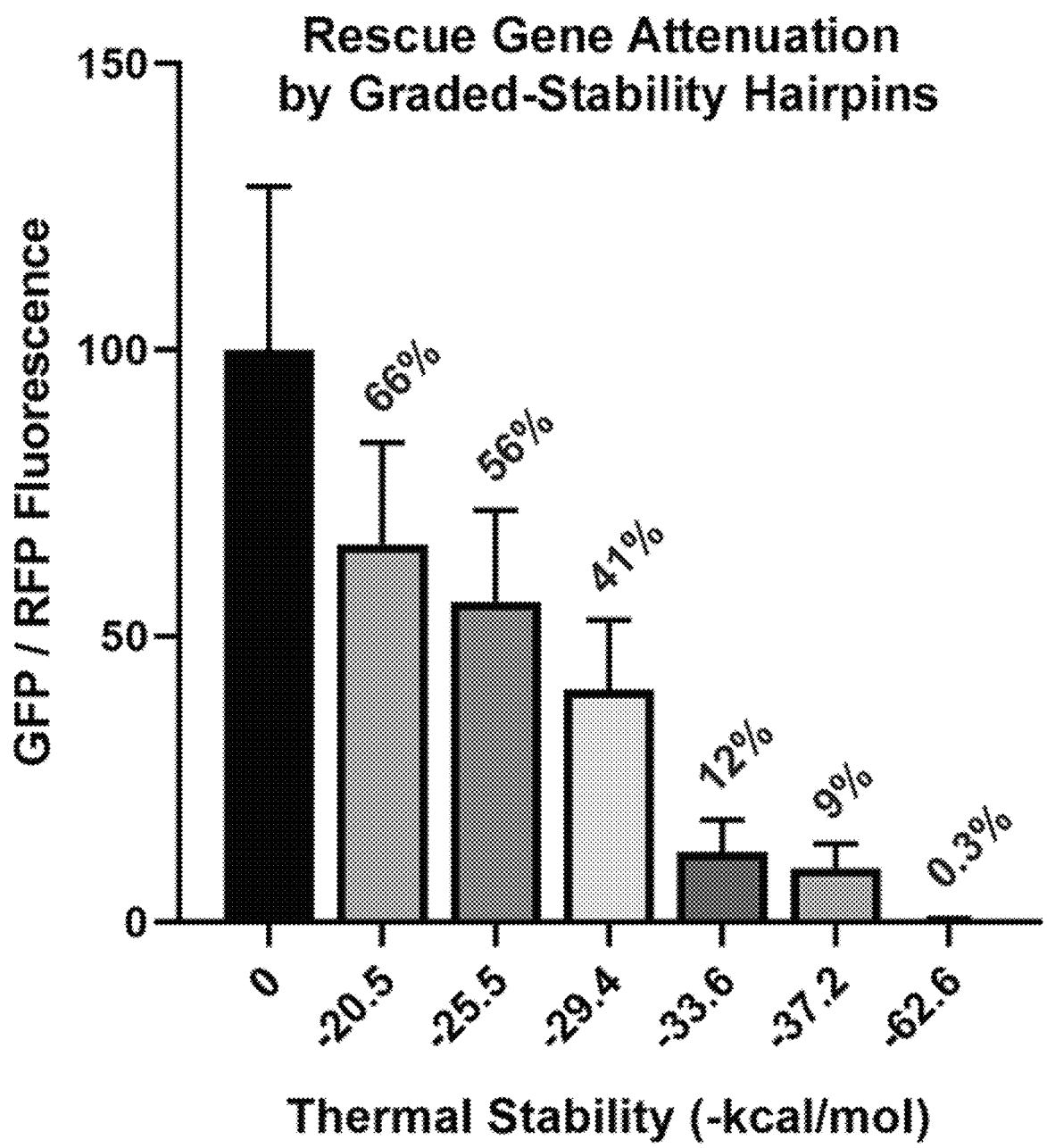
FIG. 7 shows quantification of increasingly stable hairpins compared to unattenuated (no hairpin) control.

FIG. 7 shows quantification of increasingly stable hairpins compared to unattenuated (no hairpin) control. Internally-ratioed GFP/RFP intensity ratios displayed as percentage of control condition mean ratio.

Figure 8:
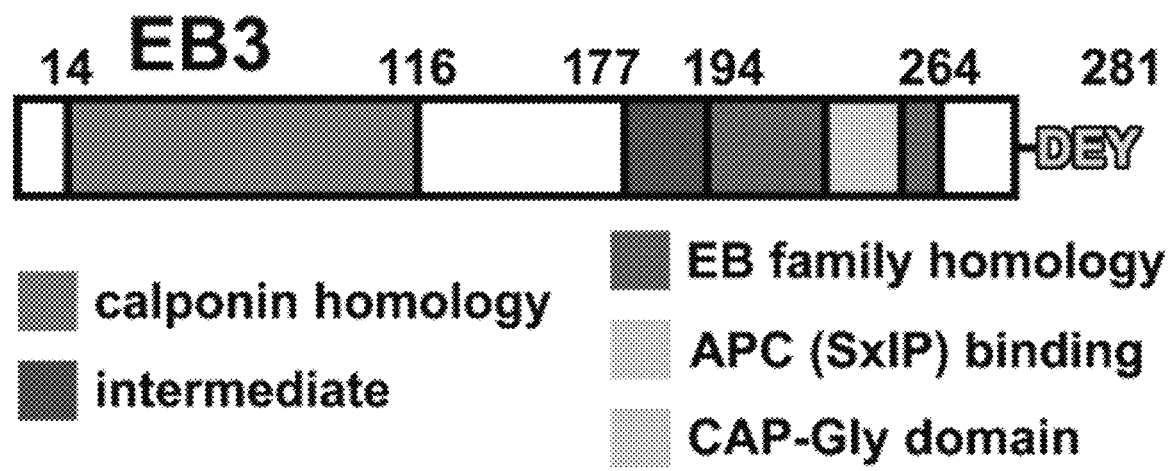
FIG. 8 shows a diagram of EB3 protein amino acid sequence with functional subdivisions outlined.

FIG. 8 shows a diagram of EB3 protein amino acid sequence with functional subdivisions outlined. "Intermediate" EB3 region highlighted in red (177-194aa) is theorized to contribute to microtubule (MT) entry into dendritic spines by interaction with spine-resident protein drebrin.

Figure 9:
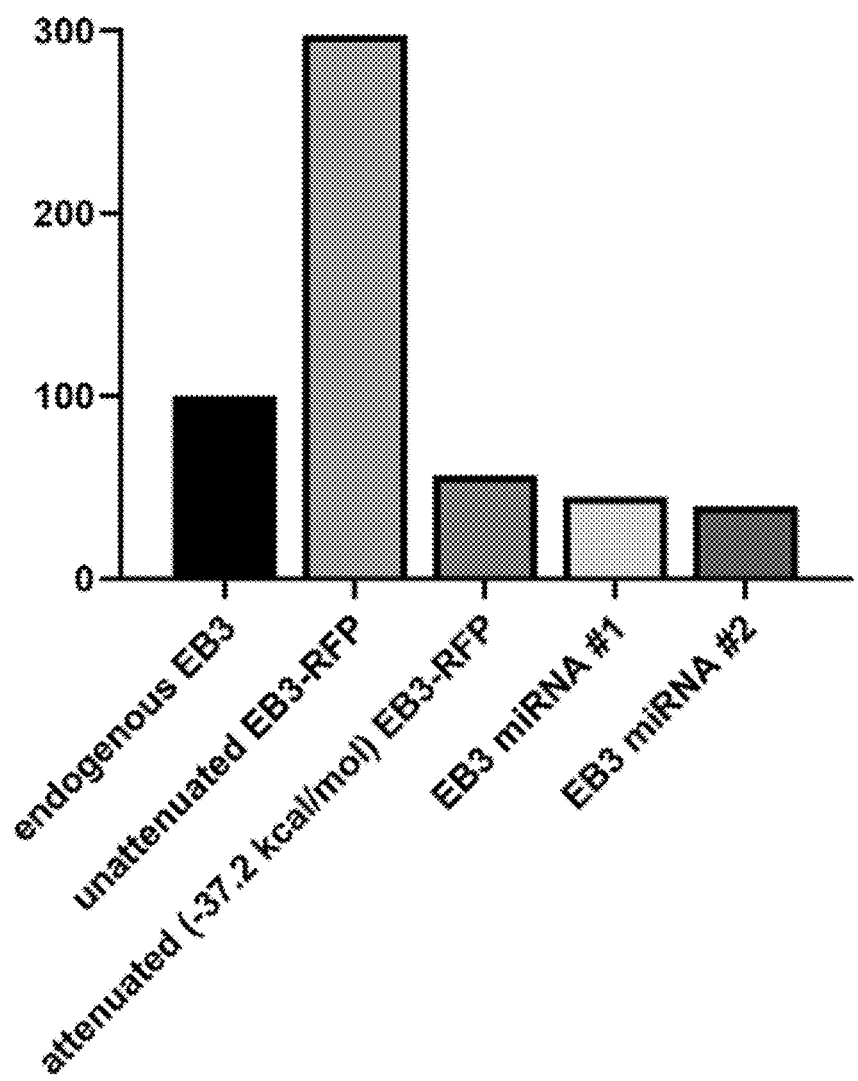
FIG. 9 shows quantification of Western blot analysis of EB3 protein content after transfection with an unattenuated vector containing EB3-RFP, an attenuated vector containing EB3-RFP and two different EB3 mRNAs.

FIG. 9 shows quantification of Western blot analysis of EB3 protein content. Rat cortical neurons were transfected, plated, and allowed to mature for 14 days before induction with doxycycline for 7 days, followed by collection of lysate for Western blot analysis. Four EB3-RFP expressing plasmids were compared. Two conditions featured non-targeting miRNA (X), one without a rescue gene (0/miRNA X) and one with −37.2 kcal/mol attenuated rescue gene (−37.2/miRNA X) to compare attenuation directly. Two additional plasmids featured miRNA (targets #1, #2) targeting of the rat EB3 3' UTR (−37.2/miRNA 1 and −37.2/iRNA 2) to determine the proportion of EB3 silenced versus EB3-RFP expressed. EB3 has a molecular weight of 32 kDa, whereas RFP (mScarlet) is 25 kDa, therefore rescue expression of EB3-RFP appears at 57 kDa and is easily differentiated from endogenous. Unattenuated expression of EB3 by the tet-ON promoter was nearly three-fold higher (298%) than endogenous levels. Attenuated mRNA yielded only 57% endogenous expression levels, six-fold less EB3-RFP than unmodified transcript. Endogenous EB3 was reduced 45% by miRNA #1, and 40% by miRNA #2. All measurements in are underestimates due to sparse transfection (~50%) efficiency in neurons. Thus, unattenuated expression of EB3-RFP is expected to be roughly 600% higher than endogenous, attenuated EB3-RFP expression 100% of endogenous, and miRNA is expected to effectively eliminate endogenous EB3 transcript in transfected cells.

Figure 10:
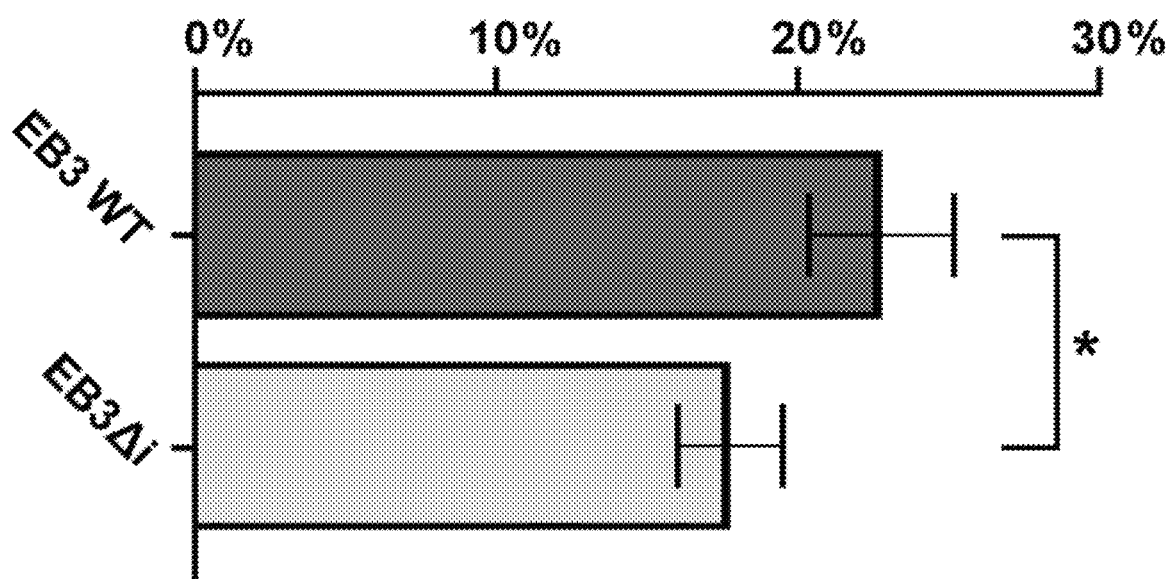
FIG. 10 shows that removal of the intermediate "i" region (177-194aa) of EB3 decreases the percent of spines invaded by MTs significantly. EB3 (22.7%±2.3, n=26), EB3Δi (17.8%±1.8, n=24, 78% of baseline, p=0.0498).

FIG. 10 shows removal of the EB3 intermediate "i" region (177-194aa) decreases the percent of spines invaded by MTs significantly. EB3 (22.7%±2.3, n=26), EB3Δi (17.8%+1.8, n=24, 78% of baseline, p=0.0498). Student's T-test, graph shows mean±SEM, * p<0.05.

In total, FIGS. 5 through 10 demonstrate replacement of endogenous protein with physiologically-matched expression of a "rescue" gene. In FIG. 10 a deficit is introduced by replacement of endogenous protein with an experimentally generated functional mutant gene. This method can also be applied to replace spontaneously occurring or inherited mutant genes with normal versions, as in the correction of diseases of genetic etiology.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. An expression cassette for gene silencing and replacement of a target protein, comprising, in operable communication,
   a promoter,
   an expression attenuator, wherein the expression attenuator comprises one or more 5'UTR hairpins, a pseudoknot, a viral or cellular internal ribosomal entry site (IRES), an RNA G-quadruplexe (RG4s), an upstream open reading frames (uORF), or an upstream start codon (uAUG),
   a nucleotide sequence encoding a gene for the replacement target protein, and
   an shRNA sequence for knockdown of an endogenous variant of the target protein,
   wherein the promoter, the expression attenuator, the nucleotide sequence encoding the gene for the replacement target protein, and the shRNA are expressed as a single transcript.

2. The expression cassette of claim 1, wherein the promoter is a constitutive promoter or an inducible promoter, wherein, when the promoter is an inducible promoter, transcription of the single transcript is controlled by the presence of an inducer for the inducible promoter.

3. The expression cassette of claim 1, wherein the expression cassette further comprises a transactivator gene for the inducible promoter, wherein the transactivator gene for the inducible promoter is operably linked to a constitutive promoter.

4. The expression cassette of claim 3, wherein the inducible promoter is a tetracycline-responsive promoter.

5. The expression cassette of claim 1, wherein the expression attenuator comprises one or more 5'UTR hairpins, wherein the number and/or stability of 5' UTR hairpins tunes the level of translation of the replacement target protein.

6. The expression cassette of claim 1, wherein the shRNA sequence is in the form of a precursor molecule comprising the sequence of the shRNA and a microRNA.

7. The expression cassette of claim 1, wherein the target protein comprises a developmentally regulated protein, or a protein wherein expression of the protein interferes with normal cell division.

8. The expression cassette of claim 1, further comprising an operably linked IRES upstream of a reporter gene.

9. An expression vector comprising the expression cassette of claim 1.

10. The expression vector of claim 9, comprising nucleic acid sequences from Moloney murine leukemia virus, Murine stem cell virus, Harvey murine sarcoma virus, murine mammary tumor virus, Rous sarcoma virus, adenovirus, adeno-associated virus, an SV40-type virus, a polyoma virus, Epstein-Ban virus, a papilloma virus, a herpes virus, a vaccinia virus, polio virus, a lentiviruses, or an RNA virus.

11. A cell comprising the expression vector of claim 9.

12. The cell of claim 11, comprising primary neuronal cells, astrocytes, oligodendrocytes, or cardiomyocytes.

13. The cell of claim 11, comprising B35 rat neuroblastoma cells, Cos 7 monkey kidney cells, HEK human embryonic kidney cells, CAD mouse Cath.a-differentiated catecholaminergic neuron-like cells, or PC12 rat pheochromocytoma neuron-like cells.

14. A method of silencing and replacement of a target gene in a cell in culture, comprising
   transforming the cell with the expression vector of claim 8, and
   optionally applying to the cell an inducer when the promoter is an inducible promoter to provide expression of the single transcript, wherein expression of the shRNA silences the expression of the endogenous variant of the target protein, and expression of the coding sequence for the replacement target protein provides the replacement target protein in the cell.

15. The method of claim 14, wherein the cell is a primary neuronal cell, an astrocyte, an oligodendrocyte, or a cardiomyocyte.

16. The method of claim 15, wherein the transforming is done one or more weeks prior to applying the inducer.

17. The method of claim 14, wherein the cell comprises B35 rat neuroblastoma cells, Cos 7 monkey kidney cells, HEK human embryonic kidney cells, CAD mouse Cath.a-differentiated catecholaminergic neuron-like cells, or PC12 rat pheochromocytoma neuron-like cells.

18. A therapeutic method, comprising administering to a subject in need thereof the expression vector of claim 9.

19. The method of claim 18, wherein the subject is suffering from Amyotrophic Lateral Sclerosis Disease, Leukodystrophy Disease, Alzheimer's Disease, or Parkinson's Disease.

20. A therapeutic method, comprising administering to a subject in need thereof the cell of claim 11.

21. The method of claim 20, wherein the subject is suffering from Amyotrophic Lateral Sclerosis Disease, Leukodystrophy Disease, Alzheimer's Disease, or Parkinson's Disease.

* * * * *